US005462733A

United States Patent [19]
Edelson et al.

[11] Patent Number: 5,462,733
[45] Date of Patent: Oct. 31, 1995

[54] IMMUNE SYSTEM MODULATION USING PSORALENS ACTIVATED WITH VISIBLE LIGHT

[75] Inventors: Richard L. Edelson, Westport; Francis P. Gasparro, Hamden, both of Conn.

[73] Assignee: Yale University, New Haven, Conn.

[21] Appl. No.: 13,831

[22] Filed: Feb. 4, 1993

[51] Int. Cl.$^6$ ............................ A61K 35/14; A61K 35/26
[52] U.S. Cl. ........................ 424/93.71; 424/534; 424/577; 435/2; 604/4
[58] Field of Search ................................. 424/93 V, 577, 424/184.1, 278.1, 93.71, 534; 435/2; 604/4

[56] References Cited

U.S. PATENT DOCUMENTS

| | | | |
|---|---|---|---|
| 4,684,521 | 8/1987 | Edelson | 424/101 |
| 4,838,852 | 6/1989 | Edelson et al. | 604/4 |
| 5,114,721 | 5/1992 | Cohen et al. | 424/534 |
| 5,116,864 | 5/1992 | March et al. | 514/455 |
| 5,147,289 | 9/1992 | Edelson | 604/4 |
| 5,256,648 | 10/1993 | Gasparro et al. | 435/172.3 |

OTHER PUBLICATIONS

Edelson, R., "Photopheresis: A Clinically Relevant Immunobiologic Response Modifier," Annals of N.Y. Academy of Sciences 636:154–164 (1991).
Gasparro, F., et al., "Cell membrane DNA: a new target for psoralen photoadduct formation," Photochem. Photobiol. 52:315–321 (1990).
Cimino, G. D., et al., "Psoralens as photoactive probes of nucleic acid structure and function: organic chemistry, photochemistry, and biochemistry," Ann. Rev. Biochem. 54:1151–1193 (1985).
Kanne, D., et al., "Psoralen–deoxyribonucleic acid photoreaction Characterization of the monoaddition products from 8–methoxypsoralen and 4,5', 8–trimethylpsoralen," Biochemistry 21:861–871 (1982).
Edelson, R., "Light–activated Drugs," Scientific American 256(8): 68–75 (1988).
Tessman, J. W., et al., "Photochemistry of the furan–side 8–methoxypsoralen–thyamine monoadduct inside the DNA helix. Conversion to diadduct and to pyrone–side monoadduct," Biochemistry 24:1669–1676 (1985).
Spielmann, H., et al., "New Methods for the Large–Scale Synthesis of Furanside Psoralen Monoadducts and Diadducts," Photochem. Photobiol. 53:1135 (1991).
Sastry, S., et al., "Recent advances in the synthesis and structure determination of site specific psoralen–modified DNA oligonucleotides," J. Photochem. Photobiol. B: Biol. 14:65–79 (1992).
Averbeck, D., "Mutagenesis by psoralens on eukaryotic cells," Photosensitization, ed. G. Moreno NATO ASI Series 15:279–291 (1988).
Averbeck D., "Recent advances in psoralen phototoxicity mechanism," Photochem. Photobiol. 50:859–882 (1989).
Sage, E., and Bredberg, A., "Damage distribution and mutation spectrum: the case of 8–methoxypsoralen plus UVA in mammalian cells," Mutation Research 263:217–222 (1991).

Cundari, E., Averbeck, D., "8–Methoxypsoralen–photoinduced DNA crosslinks as determined in yeast by alkaline step elution under different reirradiation conditions. Relation with genetic effects," Photochem. Photobiol. 48:315–320 (1988).
Bredberg, A. and Nachmansson, N., "Psoralen adducts in a shuttle vector plasmid propagated in primate cells: High mutagenicity of DNA cross–links," Carcinogenesis 8:1923–1927 (1987).
Edelson, R., et al., "Treatment of cutaneous T Cell lymphoma by extracorporeal photochemotherapy," N. Engl. J. Med. 316:297–303 (1987).
Averbeck, D., et al., "Mutagenic and recombinogenic action of DNA monoadducts photoinduced by the bifunctional furocoumarin 8–Methoxypsoralen in yeast (Saccharomyces cerevisiae)," Photochem. Photobiol. 45:371–379 (1987).
Cassier, C., et al., "Mutagenic and recombinogenic effects of DNA cross–links induced in yeast by 8–methoxypsoralen photoaddition," Photochem. Photobiol. 39:799–803 (1984).
Singhal, R. P., et al., "High–performance liquid chromatography for trace analysis of DNA and kinetics of CNA modification," BioChrom. 4:78–88 (1989).
Malane, M. and Gasparro, R., "T Cell Molecular Targets for Psoralens," Annals of N.Y. Academy of Science 636:196–208 (1991).
Sage, E., and Moustacchi, E., "Sequence context effects on 8–methoxypsoralen photobinding to defined DNA fragments," Biochemistry 26:3307–3314 (1987).
Potapenko, A. Y., "Mechanisms of photodynamic effects of furocoumarins," J. Photochem. Photobiol. B 9:1–33 (1991).
Babudri, N., et al., "Mutation Induction and killing of V79 chinese hamster cells by 8–methoxypsoralen plus near–ultraviolet light: relative effects of monoadducts and crosslinks," Mutation Res. 91:391–394 (1981).
Yang, et al., "8–MOP DNA Photoadducts in Patients Treated with 8–MOP and UVA," J. Invest. Dermatol. 92:59–63 (1989).
Deckelbaum, L., et al., "Inhibition of Smooth Muscle Cell Proliferation by 8–Methoxypsoralen Photoactivated by Visible Light," American Heart Assoc. 65th Scientific Session, abstract No. 135231 (1992).
Gasparro, F. P., et al., "Repair of 8–MOP photoadducts in human lymphocytes," DNA Damage and Repair in Human Tissues (eds. B. M. Sutherland and A. D. Woodhead) Plenum Press, N.Y., P. 137 (1990).

(List continued on next page.)

*Primary Examiner*—David L. Lacey
*Assistant Examiner*—Phillip Gambel
*Attorney, Agent, or Firm*—Wolf, Greenfield & Sacks

[57] ABSTRACT

Methods and pharmaceutical compositions for modifying the immune response of a mammal are provided. The pharmaceutical compositions include a pharmaceutically acceptable carrier and a plurality of cells containing psoralen-DNA monoadducts and substantially no psoralen-DNA crosslinks. The preparation is formed by irradiating a suspension of cells with visible light radiation in the presence of psoralen.

23 Claims, 4 Drawing Sheets

OTHER PUBLICATIONS

Bevilacqua, P. M., et al., "High performance liquid Chromatography analysis of 8-methoxypsoralen monoadducts and crosslinks in lymphocytes and keratinocytes," J. Invest. Dermatol. 97:151–155 (1991).

Gasparro, F. P., et al., "Rapid and sensitive analysis of 8-methoxypsoralen in plasma," J. Invest. Dermatol. 90:234–236 (1988).

Hosken, N. A., et al., "Class I-Restricted Presentation Occurs Without Internalization or Processing of Exogenous Antigenic Peptides," The Journal of Immunology, vol. 142:1079–1083 (Feb. 15, 1989).

Townsend, A. R. M., et al., "The Epitopes of Influenza Nucleoprotein Recognized by Cytotoxic T Lymphocytes Can be Defined with Short Synthetic Peptides," Cell, vol. 44:959–968 (Mar. 28, 1986).

Deckelbaum, et al.; Circulation, vol. 86, No. 4 Suppl. 1, p. 1227 (Abstract); 1992.

Rook; Annals of the New York Academy of Sciences, vol. 636, pp. 209–216; 1991.

Malawista, et al.; Annals of the New York Academy of Sciences, vol. 636, pp. 217–226; 1991.

Berger, et al.; Annals of the New York Academy of Sciences, vol. 636, pp. 266–278; 1991.

Bisaccia, et al.; Annals of the New York Academy of Sciences, vol. 636, pp. 321–330; 1991.

Knoblier, et al.; Annals of the New York Academy of Sciences, vol. 636, pp. 340–356; 1991.

Ullrich; Photodermatology Photoimmunology Photomedicine, vol. 8, No. 3, pp. 116–122; 1991.

Alcalay, et al.; Photochemistry & Photobiology, vol. 50, No. 2, pp. 217–220; 1989.

Cundari, et al.; Mutation Research, vol. 264, pp. 97–102; 1991.

5,462,733

IMMUNE SYSTEM MODULATION USING PSORALENS ACTIVATED WITH VISIBLE LIGHT

GOVERNMENT SUPPORT

This invention was made with government support under Contract. No. 2R01CA43058-09A1 awarded by the National Institutes of Health. The government has certain rights in the invention.

FIELD OF THE INVENTION

This invention relates to methods and pharmaceutical compositions for augmenting an immune response. The methods include irradiating cells with visible light in the presence of psoralen molecules.

BACKGROUND OF THE INVENTION

The psoralens are a group of photoreactive compounds that are activated by radiation falling within a broad range of wavelengths. Photoactivation of a psoralen molecule yields a transient species which is capable of covalently binding to a cellular target molecule in a manner which severely interrupts cellular function. The transient species remains reactive for microseconds, long enough to be chemically reactive and short enough so that, for practical purposes, once the source of irradiation is turned off, the unbound psoralen reverts to its inert form. As a consequence of these unique characteristics, psoralens provide the clinician with a class of pharmacologic agents having high chemotherapeutic potency, but only where and when the psoralens come in contact with light of an appropriate wavelength (Edelson, R., "Photopheresis: A Clinically Relevant Immunobiologic Response Modifier", *Annals of N.Y. Academy of Sciences* 636:154–164 (1991)).

one of the most widely used psoralens, and the only psoralen currently approved for clinical use, is 8-methoxypsoralen (8-MOP). 8-MOP is a linear furocoumarin and has an absorption spectrum which shows substantial absorption of energy at wavelengths between about 200 nm and 320 nm, a precipitous drop in absorption at wavelengths between 320 and 400 nm and very little absorption at wavelengths greater than 400 nm (visible wavelengths). In view of these well known absorption characteristics, psoralens historically have been activated by energy in the ultraviolet end of the energy spectrum.

In the presence of ultraviolet A radiation (UVA, 320 nm–400 nm), 8-MOP is capable of reacting with a wide spectrum of target molecules, e.g., cellular DNA, to form a mixture of photoadducts. Recently, Gasparro, et al., demonstrated that a form of DNA located on the cell surface, cell membrane DNA (CM-DNA), could be photomodified by 8-MOP in the presence of ultraviolet radiation (Gasparro, F., et al., "Cell membrane DNA: a new target for psoralen photoadduct formation", *Photochem. Photobiol.* 52:315–321 (1990). In a follow up study, Perez, et al., demonstrated that 8-MOP photomodified CM-DNA appears to play a role in immunologically mediated events (Perez, M. I., et al., "DNA associated with the cell membrane is involved in the inhibition of the skin rejection response induced by infusions of photodamaged alloreactive cells that mediate rejection of skin allograft", *Photochem. Photobiol.* 58:839–849 (1992).

In addition, numerous studies have reported on the effects of 8-MOP and ultraviolet A radiation on amino acids and proteins, although no 8-MOP amino acid adduct has been fully characterized (Midden, W. R., "Chemical mechanisms of the bioeffects of furocoumarins: the role of reactions with proteins, lipids, and other cellular constituents", *Psoralen-DNA Photobiology* (Edited by F. P. Gasparro), Vol. II:1–19, CRC Press Boca Raton, Fla. (1988) and references therein; Schlavon, O. and Veronese, F., "Extensive crosslinking between subunits of oligomeric proteins induced by furocoumarins plus UV-A irradiation," *Photochem. Photobiol.* 43:243–246 (1986); Granger, M. and Helene, C., "Photoaddition of 8-methoxypsoralen to *E. coli* DNA polymerase 1. Role of psoralen photoadducts in the photosensitized alterations of pol 1", *Photochem. Photobiol.* 38:563–568 (1983); Megaw, J., et al., "NMR analyses of tryptophan-8-methoxypsoralen photoreaction products formed in the presence of oxygen", *Photochem. Photobiol.* 32:265–269 (1990)). Midden, et al. and Caffieri, et al. have independently characterized psoralen lipid photoadducts. (Midden, W. R., *Psoralen-DNA Photobiology*, supra.; Specht, K. G., et al., "A new biological target of furocoumarins: photochemical formation of covalent adducts with unsaturated fatty acids," *Photochem. Photobiol.* 47:537–541 (1989)) (Caffieri, S., et al., "Formation of photoadducts between unsaturated fatty acids and furocoumarins", *Med. Biol. Environ.* 15:11–14 (1987)). However, only psoralen-DNA photoadducts have been fully characterized (Cimino, G. D., et al., "Psoralens as photoactive probes of nucleic acid structure and function: organic chemistry, photochemistry, and biochemistry", *Ann. Rev. Biochem.* 54:1151–1193 (1985); Kanne, D., et al., "Psoralen-deoxyribonucleic acid photoreaction. Characterization of the monoaddition products from 8-methoxypsoralen and 4,5',8-trimethylpsoralen", *Biochemistry* 21:861–871 (1982); Tessman, J. W., et al., "Photochemistry of the furan-side 8-methoxypsoralen-thymine monoadduct inside the DNA helix. Conversion to diadduct and to pyrone-side monoadduct", *Biochemistry* 24:1669–1676 (1985)).

There are three principal types of psoralen-DNA photoadducts: furan ring-DNA monoadducts (4', 5'-monoadducts or 4',5'-MA), pyrone (coumarin) ring-DNA monoadducts (3,4-monoadducts or 3,4-MA), and psoralen-DNA crosslinks. As used herein, the term monoadduct refers to a photoreaction product in which the reactive group of a target molecule, such as a pyrimidine base of DNA, is covalently coupled to either the furan ring or the pyrone ring of a psoralen molecule. The terms psoralen-crosslink or psoralen-diadduct refer to a photoreaction product in which the psoralen molecule is covalently coupled through both the furan ring and the pyrone ring to two different reactive groups of at least one target molecule, e.g., the crosslink is formed between two pyrimidine bases located on different strands of a DNA double helix.

A diverse population of psoralen-DNA photoadducts is formed as a result of the sequential absorption of photons by psoralen and psoralen-monoadducts. Upon absorbing a first photon of ultraviolet A (UVA), 8-MOP is activated to a transient species which forms a covalent bond to a reactive group of a target molecule, e.g., a pyrimidine base of a DNA, to form a psoralen-DNA monoadduct. Theoretically, either ring (furan or pyrone) may be activated with UVA radiation to form the psoralen-DNA monoadduct.

Psoralen monoadducts represent a relatively small percentage (less than 50%) of the total photoadducts formed upon activation of psoralen under photochemotherapeutic reaction conditions, such as those used in photopheresis (described below). This is because the monoadducts are capable of absorbing a second photon of radiation to form a psoralen-DNA crosslink between reactive groups of the target. In general, when the target molecule is DNA, a psoralen crosslink is formed between pyrimidine bases located on two different strands of a DNA helix. As a result of crosslink formation, DNA replication is prevented. In effect, the psoralens extend the range of wavelengths that can be used to photochemically damage DNA from wavelengths less than about 310 nm (at which wavelengths DNA is subject to direct photochemical damage from the radiation) to the long-wavelength ultraviolet (UVA wavelengths, 320–400 nm).

The synthesis and characterization of the three principal psoralen-DNA photoadducts formed between HMT 4'-(hydroxymethyl)-4,5',8-trimethylpsoralen (HMT, a synthetic derivative of 8-MOP), and a low molecular weight synthetic oligonucleotide duplex have been described (Spielmann, H. et al., "New Methods for the Large-Scale Synthesis of Furanside Psoralen Monoadducts and Diadducts", *Photochem. Photobiol.* 53:1135 (1991)). Spielmann, et al. report that reaction of a DNA 12mer (a DNA oligomer containing 12 bases) and a complementary DNA 8mer (8 bases) with HMT, in the presence of krypton laser irradiation at 406.7 nm, yielded 14% 12mer furan ring monoadducts and 10% 8mer furan ring monoadducts. Irradiation of the above-described oligomers and HMT in the presence of an argon ion laser (wavelength=366 nm) yielded between 50–80% psoralen-DNA crosslinks (diadducts).

In a related work, Sastry, et al. prepared the above-described photoadducts by reacting an excess amount of psoralen with oligonucleotide duplex, i.e., $1.6\times10^{-4}$M HMT (48 ug/ml) to $0.4\times10^{-4}$M oligonucleotide duplex, in the presence of a krypton (406.7 nm or 413 nm) or argon (364 nm) laser (Sastry, S., et al., "Recent advances in the synthesis and structure determination of site specific psoralen-modified DNA oligonucleotides", *J. Photochem. Photobiol. B: Biol.* 14:65–79 (1992)). Sastry, et al. report that irradiation of the HMT/oligonucleotide reaction mixture at 406.7 nm yielded a mixture of furan ring-oligonucleotide monoadducts and unmodified oligonucleotides. Pyrone ring monoadducts were not detected when the krypton laser was used to synthesize monoadducts at the longer wavelength. Irradiation of the oligonucleotide duplex in the presence of HMT at 364 nm with an argon laser yielded an HMT-oligonucleotide duplex crosslink. Pyrone ring-oligonucleotide monoadducts were produced from the HMT-crosslink by reversing the furan ring-duplex bond under basic conditions.

It is not clear whether the photoadducts observed by Sastry, et al. would in fact be formed under typical photochemotherapeutic conditions, e.g., irradiation of a heterogeneous preparation of cells in the presence of a substantially lower psoralen concentration (1 ug/ml). 8-MOP is significantly less soluble than HMT and cannot be obtained in solution at the concentration used by Sastry, et al. Moreover, unlike conventional photopheresis, the Sastry, et al. photochemical reaction contained a homogeneous population of target molecules in the absence of other potentially interfering cellular components. In view of the multitude of potential reactions between psoralen and the array of molecules present in a photopheresis cell preparation ("T Cell Molecular Targets for Psoralens", *Annals of N.Y. Academy of Science* 636:196–208 (1991), Malane, M. and Gasparro, F.), it is unlikely that the photoadducts described by Sastry, et al. would be formed under typical photochemotherapeutic conditions.

Although long wavelength ultraviolet radiation (UVA, 320–400 nm) and 8-methoxypsoralen (8-MOP) is an established photochemotherapy for treating disorders of the immune system, the molecular basis for the therapeutic effect of psoralen photochemotherapy has not been elucidated. Formation of psoralen-DNA photoadducts (monoadducts and crosslinks) has been presumed to be responsible for the efficacy of these therapies. The therapeutic effects of psoralen photochemistry may be dependent upon the class of adduct formed as well as upon the DNA context of the adduct (Averbeck, D., "Mutagenesis by psoralens on eukaryotic cells", *Photosensitization*, ed. G. Moreno NATO ASI Series 15:279–291 (1988); Averbeck, D., "Recent advances in psoralen phototoxicity mechanism", *Photochem. Photobiol.* 50:859–882 (1989) Sage, E., and Bredberg, A., "Damage distribution and mutation spectrum: the case of 8-methoxypsoralen plus UVA in mammalian cells", *Mutation Research* 263:217–222 (1991)); Cundari, E., Averbeck, D., "8-Methoxypsoralen-photoinduced DNA crosslinks as determined in yeast by alkaline step elution under different reirradiation conditions. Relation with genetic effects", *Photochem. Photobiol.* 48:315–320 (1988); Bredberg, A. and Nachmansson, N., "Psoralen adducts in a shuttle vector plasmid propagated in primate cells: High mutagenicity of DNA cross-links," *Carcinogenesis* 8:1923–1927 (1987); Averbeck, D., et al., "Mutagenic and recombinogenic action of DNA monoadducts photoinduced by the bifunctional furocoumarin 8-Methoxypsoralen in yeast (*Saccharomyces cerevisiae*)", *Photochem. Photobiol.* 45:371–379 (1987); Cassier, C., et al., "Mutagenic and recombinogenic effects of DNA cross-links induced in yeast by 8-methoxypsoralen photoaddition", *Photochem. Photobiol.* 39:799–803 (1984)), Shinghal, R. P., et al., "High-performance liquid chromatography for trace analysis of DNA and kinetics of CNA modification", *BioChrom.* 4:78–88 (1989); Sage, E., and Moustacchi, E., "Sequence context effects on 8-methoxypsoralen photobinding to defined DNA fragments", *Biochemistry* 26:3307–3314 (1987)).

The ability of a cell line to repair lesions also affects the toxicity and mutagenicity of psoralen-DNA photoadducts (Potapenko, A. Y., "Mechanisms of photodynamic effects of furocoumarins", *J. Photochem. Photobiol. B.* 9:1–33 (1991); Babudri, N., et al., "Mutation Induction and killing of V79 chinese hamster cells by 8-methoxypsoralen plus near-ultraviolet light: relative effects of monoadducts and crosslinks", *Mutation Res.* 91:391–394 (1981)). Accordingly, cellular mutations may arise as a consequence of misrepair or misreading during mitosis of the psoralen-DNA lesion. Indirect evidence suggests that the psoralen-DNA crosslink may be the most mutagenic of the psoralen-DNA lesions (Averbeck, D., *Photosensitization*, NATO ASI Series 15:279–291 (1988) supra; Cundari, E., Averbeck, D., *Photochem. Photobiol.* 48:315–320 (1988) supra; Bredberg, A. and Nachmansson, N., *Carcinogenesis* 8:1923–1927 (1987) supra; Sage, E., Bredberg, A., *Mutation Research* 263:217–222 (1991) supra; Cassier, C., et al., *Photochem. Photobiol.* 39:799–803 (1984) supra).

Psoralen photochemotherapy has been shown to alter cellular antigenicity (Malane, M., et al., "Treatment with 8-methoxypsoralen (8-MOP) and ultraviolet A (UVA) radiation enhances immune recognition in a murine mastocytoma model", *J. Invest. Dermatol.* 98:554A (1992)). It is believed that psoralen photoadduct formation modulates the immune system response by causing cellular mutations which result in phenotypic cellular changes. Accordingly, psoralen photochemotherapy has been directed to (1) regulating an aberrant immune system response via modification of the T cell surface receptor, e.g., by inducing presentment of a novel T cell receptor or (2) augmenting the immune system response to a specific antigen, e.g., by inducing presentment of novel antigenic peptides associated with major histocompatibility complex molecules on the cell surface. Several studies, described herein, have suggested that the ability of the immune system to recognize the receptor of an aberrant T cell clone as antigenic makes possible the vaccination of a patient against a pathogenic clone of T cells, i.e., by administering to the patient photochemically modified aberrant T cells.

Cutaneous T cell lymphoma (CTCL) is an example of an immune system disease that is caused by a massive expansion of a single clone of aberrant T cells. Extracorporeal photochemotherapy ("photopheresis") for the treatment of cutaneous T cell lymphoma has been described (Edelson, R., "Light-activated Drugs", *Scientific American* 256(8): 68–75 (1988); Edelson, R., *Annals of N.Y. Academy of Sciences* 636:154–164 (1991) supra. The treatment comprises isolating the patient's T cells, irradiating the cells with ultraviolet A radiation in the presence of a photoactivatable agent, e.g., 8-MOP, and reinfusing the damaged T cells. This therapy reportedly results in selective destruction of the malignant T cell clone.

Conventional photopheresis (irradiation with ultraviolet A radiation in the presence of 8-MOP) has also been used for the treatment of several autoimmune disorders, including pemphigus vulgaris and systemic sclerosis (Rook, A., "Photopheresis in the Treatment of Autoimmune Disease: Experience with Pemphigus Vulgaris and Systemic Sclerosis", *Annals of N.Y. Academy of Science* 636:209–216 (1991) and rheumatoid arthritis (Malawista, S., et al., "Photopheresis for Rheumatoid Arthritis", *Annals of N.Y. Academy of Science* 636:217–226 (1991). Long wavelength ultraviolet radiation and 8-MOP have also been used as a photochemotherapy for the treatment of psoriasis (Parrish, J., et al., "Photochemotherapy of psoriasis with oral methoxsalen and long wavelength ultraviolet light", *N. Engl. J. Med.* 29:1207–1211 (1974)) and in a preliminary study to evaluate the potential therapeutic value of photopheresis in seven patients with AIDS-related complex (ARC) (Bisaccia, E. et al., "Viral-Specific Immunization in AIDS-Related Complex by Photopheresis", *Annals of N.Y. Academy of Science* 636:321–330 (1991).

Photopheresis also has been used prophylactically to prevent graft rejection by injecting into mice a preparation containing Photoinactivated Effector T ("PET") cells (Perez, M. et al., "Inhibition of Antiskin Allograft Immunity Induced by Infusions with Photoinactivated Effector T Lymphocytes (PET Cells); "The Congenic Model", *Transplantation* 51:1283–1289 (1991). To prepare the PET cells, T cell clones mediating skin graft rejection were expanded in vivo and photoinactivated by ultraviolet irradiation in the presence of 8-MOP. Perez, et al. report that this procedure results in the adoptive transfer of tolerance for skin allotransplantation, as demonstrated by prolongation of allograft survival in the recipients of PET cells.

The above-described photopheresis procedures have also been used to augment the immune system response to a specific antigen. In particular, U.S. Pat. No. 4,838,852, issued to Edelson et al. (hereinafter Edelson '852), the contents of which are incorporated herein by reference, describes a method for enhancing the immune system response of a mammal to an antigen. The Edelson '852 method comprises (a) contacting the subject's immune system with the specific antigen for a suitable time to artificially stimulate the immune system, (b) withdrawing antigen-stimulated blood cell material from the subject, (c) treating the withdrawn material to alter the antigen-stimulated cells, and (d) returning the treated material to the subject. Edelson '852 also discloses that it may be possible to render the cells incapable of recognizing an antigen by withdrawing the blood cell-containing material from the subject, treating the withdrawn material as above, returning the treated material to the subject and then contacting the subject's immune system with a specific antigen.

U.S. Pat. No. 5,147,289, issued to Edelson (hereinafter Edelson '289), the contents of which are incorporated herein by reference, describes methods for non-specifically enhancing the immune system response of a mammal to an antigen. The method comprises (A) enhancing the immune system response by (a) withdrawing leukocyte containing material from the mammal, (b) treating the withdrawn leukocytes in a manner to alter the cells, (c) returning the treated leukocytes to the mammal and (B) artificially contacting the mammal's immune system with the antigen for a suitable period of time to stimulate an immune system response.

With respect to the Edelson '852 and '289 patents, the withdrawn leukocytes may be altered by, for example, irradiating the leukocytes with ultraviolet radiation in the presence of a photoactivatable agent, e.g., a psoralen, exposure to ultraviolet light in the absence of a photoactivatable agent, and exposure to visible light in the presence of a photoactivatable agent such as hematoporphyrin. In a preferred embodiment, the leukocytes are gently damaged by ultraviolet radiation in the presence of a psoralen.

The combination of ultraviolet radiation (320–400 nm) and 8-MOP has also been proposed as a photochemotherapeutic method for preventing restenosis in a subject undergoing vascular recanalization (U.S. Pat. No. 5,116,864, issued to March et al.). Ultraviolet radiation in the range of about 320 to about 400 nm was disclosed to activate the psoralen at the region of the recanalization. More recently, L. Deckelbaum, et al. described a method for preventing restenosis, which method includes activation of 8-MOP with visible light irradiation to inhibit smooth muscle cell proliferation (Deckelbaum, L. et al., "Inhibition of Smooth Muscle Cell Proliferation by 8-Methoxypsoralen Photoactivated by Visible Light", American Heart Assoc. 65th Scientific Session, abstract no. 135231 (1992)). Bovine aortic smooth muscle cells were exposed to 1 ug/ml 8-MOP and irradiated with a broadband blue light source (peak wavelength=420 nm, bandwidth=34 nm). The formation of 8-MOP-DNA adducts in smooth muscle cells was confirmed by HPLC analysis.

None of the above-cited references and patents disclose a method for modulating an immune system response, which method comprises administering a cell suspension containing a plurality of non-lethal psoralen-photoadducts (monoadducts) and substantially no lethal psoralen-photoadducts (crosslinks). Accordingly, there is still a need for psoralen photoactivation methods which permit formation of photochemically modified cells containing psoralen-DNA monoadducts under conditions which generate virtually no psoralen-DNA crosslinks. The photoactivation method would be less toxic to the irradiated cells in comparison with photopheresis conditions currently employed.

SUMMARY OF THE INVENTION

The present invention provides methods for forming a suspension of cells containing cellular nucleic acid-psoralen monoadducts and pharmacological compositions containing the same. The cell suspension is administered to a mammal to modulate the mammal's immune system response.

According to one aspect of the invention, a method for forming a suspension of cells containing cellular nucleic acid-psoralen monoadducts is provided. The method comprises contacting a suspension of cells containing cellular nucleic acid molecules with a plurality of psoralen molecules to form a psoralen-cell suspension and extracorporeally irradiating the psoralen-cell suspension with visible light to form a plurality of cellular nucleic acid-psoralen monoadducts. The use of visible wavelength radiation (400 nm to 700 nm) results in a cell suspension which is substantially free of cellular nucleic acid-psoralen crosslinks. The radiation used for photoactivation of the psoralen is in a wavelength range greater than about 400 nanometers and is preferably in a wavelength range equal to or greater than about 420 nanometers. A laser may be used to deliver high intensity radiation at the preferred visible wavelengths. In a preferred embodiment, a helium/cadmium continuous wave laser having a wavelength of 442 nanometers is used for psoralen photoactivation. A dosage in the range of about 10 to 40 J/cm$^2$ is preferred. Alternatively, a continuous wave or low power pulsed light source can be used to practice the present invention. Other suitable light sources include a mode-locked argon laser and diode lasers.

The suspension of cells may be an isolate from a source that is selected from the group consisting of blood, lymph fluid, bone marrow, lymphatic organ tissue and tissue culture. In a preferred embodiment, the cells are leukocytes, the cellular nucleic acid is DNA and the psoralen is selected from the group consisting of 8-methoxypsoralen, aminomethyltrimethylpsoralen, 5-methoxypsoralen and trimethylpsoralen. Most preferably, the cells are T cells and the psoralen is 8-methoxypsoralen.

According to another aspect of the invention, a method for making a pharmaceutical preparation for administration to a mammal is provided. The method comprises placing the above-described irradiated psoralen-cell suspension, or components of same, in a pharmaceutically acceptable carrier.

According to yet another aspect of the invention, a method for modifying the immune system response of a mammal is provided. The method comprises administering the above-described pharmaceutical preparation to the mammal, preferably to a human.

In a preferred embodiment, the pharmaceutical preparation is stored in aliquots containing an amount of cells with cellular nucleic acid-psoralen monoadducts sufficient to modify the immune response of the patient. Selection of an amount of cells necessary to augment the patient's immune response is within the capabilities of those skilled in the art without the need for undue experimentation. The amount of cells is, in part, dependent upon the patient's age, weight and medical profile. Preferably, an amount of cells ranging from a minimum of about 25,000 to a maximum of about 200×10$^6$ antigen presenting cells is sufficient to augment the immune response of the patient (Ben-Nun, A., et al., "Vaccination against autoimmune encephalomyelitis with T lymphocyte line cells reactive against myelin basic protein", *Nature* 292:60–61 (1981); Holoshitz, J., et al., "Lines of T lymphocytes induce or vaccinate against autoimmune arthritis", *Science* 219:56–58 (1983); Lider, O., et al., "Anti-idiotypic network induced by T cell vaccination against experimental autoimmune encephalomyelitis", *Science* 239:181–183 (1988); Khavari, P., et al., "Specific vaccination against photoinactivated cloned T cells", *Abstract Clin. Res.* 36:662A (1988); and Edelson, R., et al. "Treatment of cutaneous T cell lymphoma by extracorporeal photochemotherapy", *N. Engl. J. Med.* 316:297–303 (1987).

According to yet another aspect of the invention, a method for modifying the immune system response of a mammal to an antigen is provided. The method comprises withdrawing a suspension of cells containing nucleic acid molecules from the mammal, contacting the cells with a plurality of psoralen molecules to form a psoralen-cell suspension; extracorporeally irradiating the psoralen-cell suspension with visible light to form a plurality of cellular nucleic acid-psoralen monoadducts; administering the irradiated psoralen-cell suspension to the mammal and artificially contacting the mammal's immune system with the antigen for a suitable period of time to stimulate the immune system. The irradiated cell suspension contains a plurality of cellular nucleic acid-psoralen monoadducts and substantially no psoralen-nucleic acid crosslinks. In a preferred embodiment, psoralen is administered orally to the patient prior to withdrawing the suspension of cells from the mammal. The antigen is selected from the group consisting of peptides, nucleic acids, polysaccharides and analogues thereof. In a preferred embodiment, the antigen is an autologous antigen, or is associated with a variety of diseases and/or conditions including a solid tumor malignancy, an immunodeficiency disease or a hypersensitivity disease. Such antigens are known to those of ordinary skill in the art.

According to still another aspect of the invention, a pharmaceutical composition for modifying an immune system response is provided. The composition comprises a pharmaceutically acceptable carrier and a preparation of cells, the cells containing a plurality of cellular nucleic acid-psoralen monoadducts and substantially no cellular nucleic acid-psoralen crosslinks.

In a preferred embodiment, the ratio of cellular nucleic acid-psoralen monoadducts to nucleic acid-psoralen crosslinks is at least about 2 to 1, more preferably 10 to 1 and most preferably, 49 to 1. The cell suspension of the instant invention has a substantially higher proportion of psoralen-DNA monoadducts in comparison with cells that have been photochemically altered according to conventional photopheresis methods, e.g., irradiation with long wavelength ultraviolet radiation in the presence of 8-MOP. From indirect evidence, it has been inferred that the preferential formation of psoralen-monoadducts over crosslinks results in fewer lethal cell mutations. Accordingly, the pharmacological preparation of the instant invention differs from that resulting from conventional photopheresis in containing a greater number of photochemically altered, viable cells.

These and other aspects of the invention as well as various advantages and utilities will be more apparent with reference to the detailed description of the preferred embodiments and in the accompanying drawings.

BRIEF DESCRIPTION OF THE DRAWINGS

FIG. 4A illustrates the orientation of 8-MOP between adjacent bases of a DNA backbone.

DETAILED DESCRIPTION OF THE INVENTION

Figure 1:
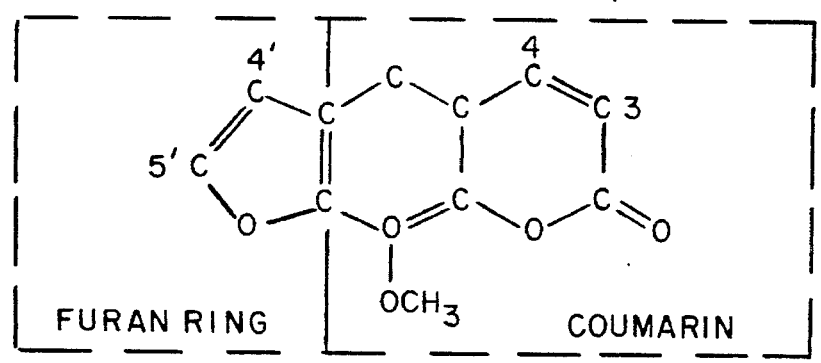
FIG. 1 illustrates the structure of 8-methoxypsoralen (8-MOP)

One method for forming a suspension of cells containing cellular nucleic acid-psoralen monoadducts comprises (a) contacting a suspension of cells containing cellular nucleic acid with a plurality of psoralen molecules to form a psoralen-cell suspension and (b) extracorporeally irradiating the psoralen-cell suspension with visible light to form a plurality of cellular nucleic acid-psoralen monoadducts. Irradiation with visible light results in a cell suspension containing primarily cellular nucleic acid-psoralen monoadducts and substantially no cellular nucleic acid crosslinks.

In general, the radiation used for photoactivation of the psoralen is in a wavelength range greater than about 400 nanometers and is preferably in a wavelength range equal to or greater than about 420 nanometers. A laser may be used to deliver high intensity radiation at the preferred visible wavelengths. In a preferred embodiment, a helium/cadmium continuous wave laser having a wavelength of 442 nanometers is used for psoralen photoactivation. A dosage in the range of about 10 to 40 J/cm$^2$ is preferred. Alternatively, a continuous wave or low power pulsed light source can be used to practice the present invention. Other suitable light sources include a mode-locked argon laser and diode lasers. In a preferred embodiment, the visible light has a wavelength of about 450 nm and an intensity of about 6mW/cm$^2$ The psoralen-cell suspension is irradiated with visible light for about 1 to about 3 hours.

The above-disclosed ranges are merely drawn to the preferred embodiments of the instant invention and are not intended to limit the scope of the invention to any particular combination of irradiation parameters. As would be apparent to one of ordinary skill in the art, and as demonstrated in Examples 3 and 4 herein, the irradiation parameters of wavelength, intensity, time of irradiation are interrelated. Accordingly, any combination of irradiation parameters which results in formation of a cell preparation containing a plurality of cellular nucleic acid-psoralen monoadducts and substantially no cellular nucleic acid-psoralen crosslinks is intended to be embraced by the instant invention. As used herein, the phrase, "substantially no crosslinks", refers to a cell suspension in which greater than 50% of the psoralen photoadducts are psoralen-monoadducts. As illustrated in the referenced Examples, substantially higher percentages of psoralen monoadducts can be obtained by selecting different irradiation parameters, quantitating the photoadducts formed thereby and systematically selecting that combination of irradiation parameters which yields the desired psoralen-monoadduct percentage (See e.g., Examples 3 and 4). For therapeutic applications, it may be desirous to have a cell preparation containing 100% psoralen-monoadducts. In contrast to the instant invention, prior art psoralen photoactivation methods, i.e., irradiation of a cell suspension with ultraviolet A radiation in the presence of psoralen, yield a cell suspension containing greater than 50% psoralen crosslinks.

In a preferred embodiment, the cells are leukocytes from human fluid samples, e.g., peripheral blood, lymph fluid, bone marrow, lymphatic organ tissue or cell cultures derived therefrom. Leukocytes are white blood cells which include lymphocytes (T cells and B cells), polymorphonuclear cells and monocytes. In a preferred embodiment, the leukocytes are T cells.

In accordance with the instant invention, the cells are photochemically altered and are administered to a subject to modify the subject's immune system response. It is believed that the damaged cells act as a non-specific adjuvant to augment the immune response. Although the cells contain various target molecules which may be photochemically altered by irradiation with visible light in the presence of a plurality of psoralen molecules, cellular nucleic acid serves as the principal target for psoralen photoadduct formation. In accordance with the instant invention, the psoralen molecules bond to pyrimidine bases in DNA to form psoralen-DNA monoadducts.

As used herein, the term psoralen refers to photoactivatable molecules containing both a furan and a pyrone ring. Psoralens are inert prior to exposure to radiation and are transiently activated to an excited state following irradiation. Due to the absorption characteristics of psoralens (discussed below), these agents historically have been activated with ultraviolet A radiation. A key aspect of the instant invention is the discovery that, despite the low extinction coefficients at visible wavelengths, visible light may be used to activate psoralen to a transient species which is capable of photochemically alkylating a target molecule, such as cellular DNA.

Figure 2:
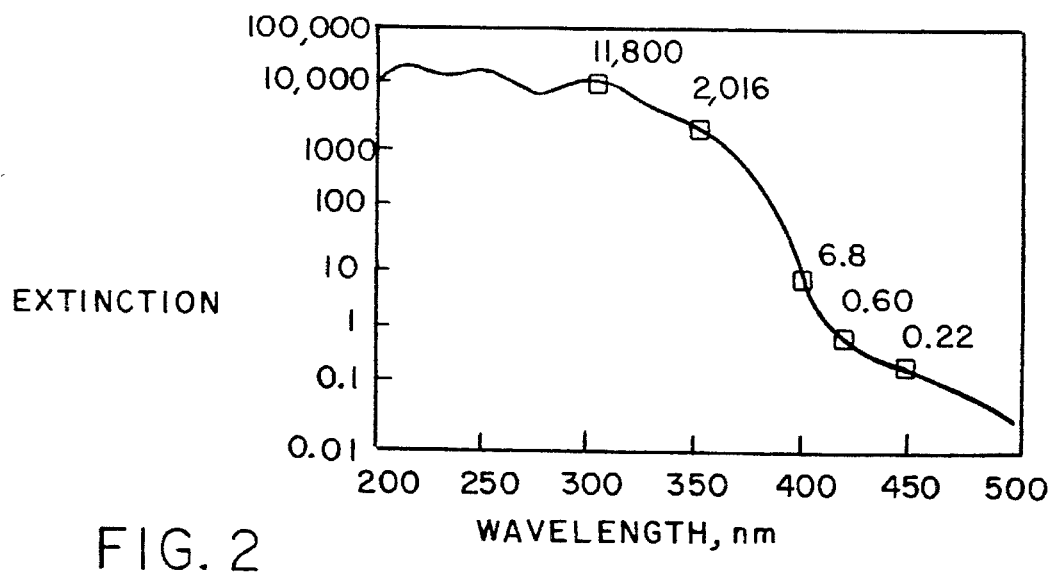
FIG. 2 illustrates the absorption spectrum of 8-methoxypsoralen.

One of the most widely used psoralens, and the only psoralen currently approved for clinical use, is 8-methoxypsoralen (8-MOP), the structure of which is shown in FIG. 1. The absorption spectrum for 8-MOP (dissolved in absolute ethanol) shows substantial absorption at wavelengths between about 200 nm and 320 nm, a precipitous drop in absorption at wavelengths between 320 and 400 nm (ultraviolet A) and very little absorption at wavelengths greater than 400 nm (FIG. 2 and Example 1). The extinction coefficients for 8-MOP at selected wavelengths (300, 350, 400, 420 and 450 nm) are included in FIG. 2 to illustrate the low but finite absorbance by 8-MOP in the visible region of the spectrum. The extinction coefficients were derived from gravimetrically determined molar concentrations of 8-MOP.

Figure 3:
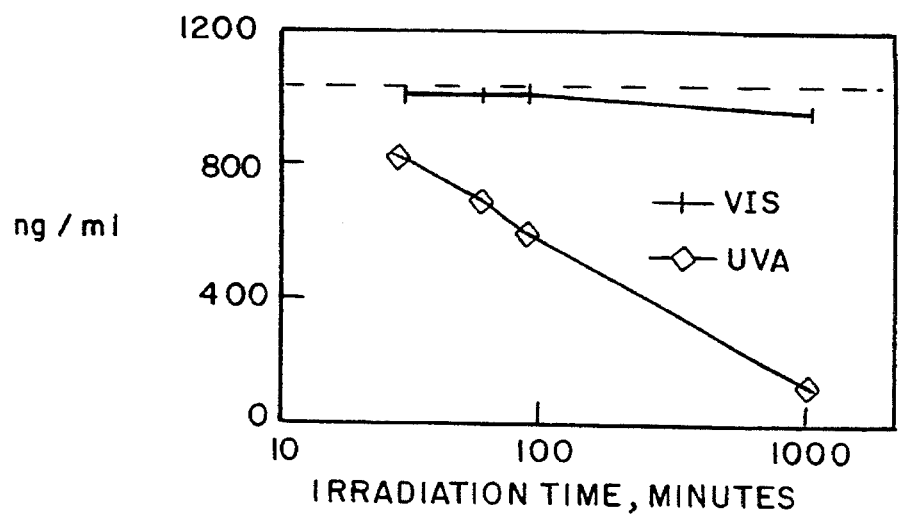
FIG. 3 illustrates the effect of 419 nm light (VIS) and ultraviolet A (UVA) radiation on 8-methoxypsoralen degradation.

By comparing the extinction coefficients at 350 nm and 420 nm (2016 and 0.60M$^{-1}$ respectively) one would predict that a nearly 3360-fold increase in radiation dose at 420 nm would be required to deliver the same number of absorbed photons (and hence induce a similar number of photoadducts) as a radiation dose at 350 nm. Surprisingly, a much smaller dose of visible radiation (20-fold) is required to form psoralen-DNA monoadducts than would be predicted based upon the extinction coefficient of 8-MOP at 419 nm (Example 2). As disclosed in Examples 2 and 3, the unanticipated efficiency of psoralen-DNA monoadduct formation under conditions of visible light irradiation is, at least in part, due to a reduced rate of psoralen and/or monoadduct degradation upon exposure to visible wavelength irradiation compared to the relatively high rate of degradation of these compounds upon exposure to ultraviolet wavelength irradiation (FIG. 3).

Figure 4A:
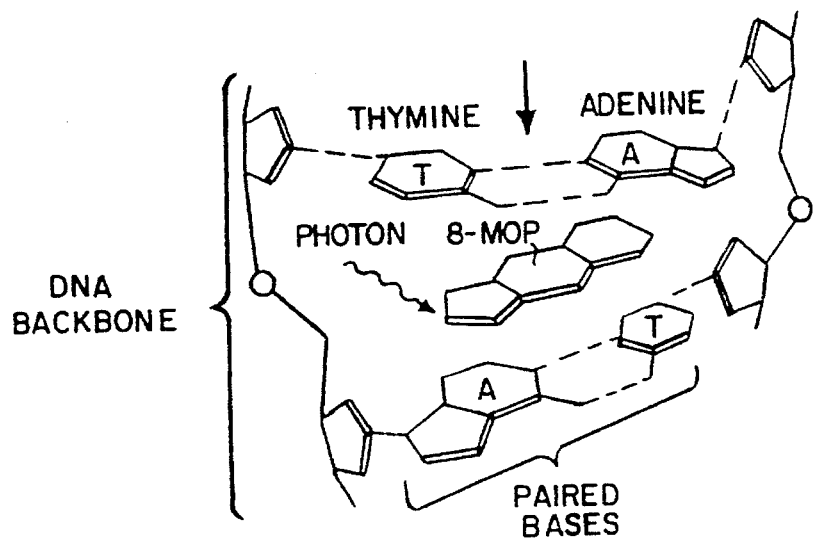
FIGS. 4A and 4B schematically illustrate formation of an 8-MOP-DNA monoadduct upon absorption of a first photon of energy.
Figure 4B:
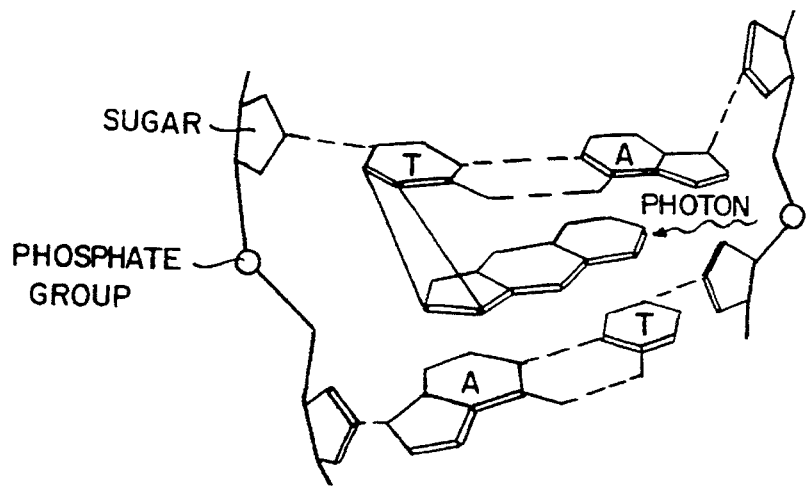
Figure 5:
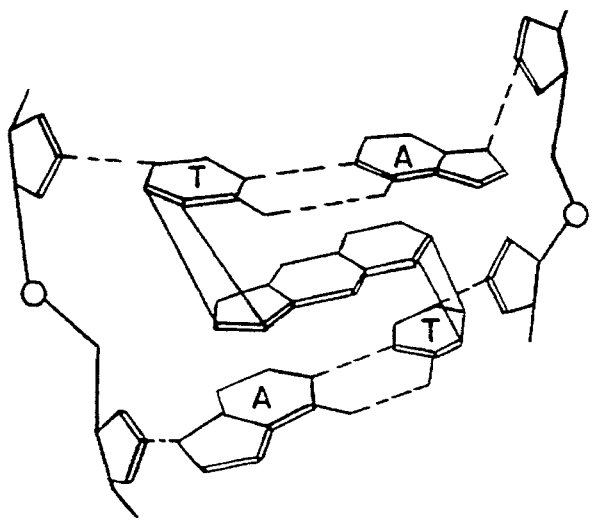
FIG. 5 schematically illustrates formation of an 8-MOP-DNA crosslink upon absorption of a second photon of energy by the 8-MOP-DNA monoadduct of FIG. 4.

FIGS. 4 and 5 schematically illustrate the formation of psoralen monoadducts and crosslinks upon absorption of a first and a second photon of radiation, respectively. The term monoadducts refers to a psoralen-modified target molecule in which the active group of the target molecule is covalently coupled to either the furan ring (4',5'-MA or 4',5'-monoadduct) or the pyrone ring (3,4-MA or 3,4-monoadduct) of psoralen. In theory, upon absorbing a first photon of light, 8-MOP covalently bonds to a pyrimidine base of DNA (FIG. 4) to form a psoralen-monoadduct. We believe that the monoadduct is incapable of absorbing a second photon of light at visible light wavelengths. Thus, irradiation of 8-MOP and DNA with visible light permits accumulation of psoralen-DNA monoadducts without the attendant formation of psoralen-DNA crosslinks.

In contrast to the instant invention, reaction of DNA and psoralen in the presence of ultraviolet A irradiation results primarily in the formation of psoralen-nucleic acid crosslinks (i.e., greater than 50% of all photoadducts) as a result of additional photon absorption by psoralen-DNA monoadducts (FIG. 5). As previously mentioned, such crosslinks currently are reported to be the most mutagenic type of psoralen-DNA lesion.

Monoclonal antibodies which recognize 8-MOP-DNA photoadducts in irradiated cells may be used to determine the optimum amount of visible light irradiation to achieve optimal psoralen-DNA monoadduct formation (see Yang et al., "8-MOP DNA Photoadducts in Patients Treated with 8-MOP and UVA", *J. Invest. Dermatol.* 92:59–63 (1989). Gasparro, et. al., also have reported methods for the quantitation of both the overall level of photoadduct formation (Gasparro, F. P., et al., "Repair of 8-MOP photoadducts in human lymphocytes" *DNA Damage and Repair in Human Tissues* (eds. B. M. Sutherland and A. D. Woodhead) Plenum Press, N.Y., p. 137 (1990)) and the extent of monoadduct and crosslink formation (Bevilacqua, P. M., et al., "High performance liquid Chromatography analysis of 8-methoxypsoralen monoadducts and crosslinks in lymphocytes and keratinocytes", *J. Invest. Dermatol.* 97:151–155 (1991)). The ratio of monoadducts and crosslinks produced upon activation of psoralen in the presence of a target molecule depends, at least in part, upon the rate of monoadduct formation relative to the rate at which the monoadduct proceeds to crosslink (Sastry, et al., supra.). Applicants have discovered that the distribution of photoadducts also depends upon the rate of psoralen and/or monoadduct degradation at the wavelength of irradiation. These degradation rates are proportional to the extinction coefficients of the psoralen and monoadduct at the wavelength at which the irradiation takes place.

The rate of psoralen and/or monoadduct degradation has not previously been considered as a factor in determining the distribution of photoadducts in a photoreaction. Measurement of the relative ability of ultraviolet A (UVA) and visible radiation to induce 8-MOP photodegradation is disclosed in Example 2 and illustrated in FIG. 3. The results indicate that shorter UVA wavelengths (320 and 340 nm, for example) much more efficiently degrade 8-MOP than longer UVA wavelengths or visible light. Thus, the shorter wavelength components of UVA radiation appear to directly degrade 8-MOP, thereby reducing the effective concentration of drug available for photoreactions with DNA. The shorter UVA wavelengths may also reduce the level of photoadduct formation by inducing the photoreversal of already formed photoadducts (Tessman, J., "Photochemistry of furan-side 8-methoxypsoralenthymidine monoadduct inside the DNA helix. Conversion to diadduct and to pyrone-side monoadduct.", *Biochem.* 24:1669–1676 (1985)).

Example 3 describes formation and quantitation of photoadducts present in bovine aorta smooth muscle cells following treatment with 8-methoxypsoralen (1000 ng/ml) and 419 nm light (up to 12 J/cm$^2$). Cellular DNA was isolated, hydrolyzed using nucleolytic enzymes and analyzed by reverse phase HPLC as described in the Example. The primary effect of using 419 nm light having an intensity of 7 J/cm$^2$ in lieu of long wavelength ultraviolet radiation was a more than tenfold reduction in the extent of crosslink formation (Example 3, Table 1). The irradiation conditions may be selected to provide 100% monoadducts (Example 4, Table 3). A reduction in crosslink formation when visible light is used for psoralen activation may also reduce the mutagenicity of 8-methoxypsoralen and hence enhance its therapeutic efficacy, e.g., by permitting photomodification of cells under non-cytotoxic conditions to produce mutant, viable cells for administration to a patient. Various assays are known to those of skill in the art for determining cell viability. For example, the relative proportions of viable and non-viable cells in a cell preparation may be determined by exposing an aliquot of the preparation to trypan blue and comparing the number of cells which exclude trypan blue with the number of cells which adsorb the dye. Viable cells have an intact membrane which acts to exclude trypan blue.

In addition to 8-methoxypsoralen (8-MOP), preferred psoralens include 4'-aminomethyl-4,5', 8-trimethylpsoralen (AMT) 5-methoxypsoralen (5-MOP) and trimethylpsoralen (TMP). AMT is a synthetic, water soluble analogue of 8-MOP. This and other synthetic water soluble analogues of 8-MOP are described in Berger et al., "The Medical and Biological Effects of Light", *Annals of N.Y. Academy of Science* 453:80–90 (1985). Some investigators have reported that 5-MOP is not as efficacious as 8-MOP in the treatment of psoriasis (Calzavara-Pinton, et al., *Exptl. Dermatol.* 1:46–51(1992)). TMP is widely used to treat vitiligo patients resulting in the repigmentation of depigmented areas of skin.

8-MOP is presently the only psoralen approved for use in clinical applications. 8-MOP may be administered orally to the patient or introduced directly into the suspension of cells. The conditions for oral administration of 8-MOP are described in U.S. Pat. No. 5,147,289, the contents of which have been incorporated herein by reference. Following oral administration, psoralens are absorbed from the digestive tract, reaching peak levels in the blood and other tissues in one to four hours and are excreted almost entirely within 24 hours.

Introduction of the psoralen molecules directly to the cell suspension offers several advantages over oral dosage administration. Dosage levels are more easily monitored and maintained in vitro. Moreover, extracorporeally administered psoralens can be attached to drug carriers that would otherwise be too toxic for oral administration. Such carriers can be used to target the agent into a specific cell or into a particular cell location, e.g., the cell nucleus to target nuclear DNA. For example, insulin has been used to carry large photoreactive molecules, e.g., fluorescein and psoralen, into activated T lymphocytes and monoclonal antibodies have been used to deliver liposomes with photoreactive pyrene incorporated into its membrane to target T cells (see Berger, C., et al., "Comparison of Synthetic Psoralen Derivatives and 8-MOP in the Inhibition of Lymphocyte Proliferation", *Annals of N.Y. Academy of Science* 453:80–90 (1985). Such carrier mediated photoactivatable drug delivery can be used in accordance with the present invention to deliver a photoactivatable drug directly to the target cell.

The invention also provides a method for making a pharmaceutical preparation for administration to a mammal. The suspension of cells containing cellular nucleic acid molecules are contacted with a plurality of psoralen molecules to form a psoralen-cell suspension. The psoralen-cell suspension is irradiated with visible light to form a cell suspension containing a plurality of cellular nucleic acid-psoralen monoadducts and substantially no cellular nucleic acid-psoralen crosslinks. The cell suspension may be placed in a pharmaceutically acceptable carrier at any stage during the photomodification reaction, e.g., before or after irradiation with visible light.

The invention further provides a method for modifying the immune system response of a mammal to an antigen. In contrast to photopheresis methods of the prior art, the present invention discloses the use of visible light radiation to photoactivate psoralen. Photopheresis procedures are described in U.S. Pat. No. 5,147,289, the contents of which have been incorporated herein by reference. Photopheresis may be performed on a continuous stream, as described in the Edelson '289 patent, or may be performed batchwise. Briefly, continuous photopheresis, as applied to the instant invention, comprises withdrawing the leukocytes from the patient, forming the suspension of cells into an extracorporeal stream, flowing the stream through a treatment chamber substantially transparent to visible light radiation, irradiating the stream in the chamber with visible light radiation in the presence of the plurality of psoralen molecules, and administering the irradiated leukocytes to the patient. Psoralen molecules may be orally administered to the patient prior to withdrawing the cell material from the patient for treatment. Alternatively, psoralen molecules may be added extracorporeally to the cell suspension.

Photopheresis requires that the above-described pharmaceutical composition be administered to the mammal to augment the mammal's immune response. In an alternative embodiment, the irradiated cells containing the nucleic acid-psoralen monoadducts are stored in aliquots containing an amount of cells sufficient to augment the immune response of the mammal.

As described above, determination of the amount of cells necessary to augment the patient's immune response is within the ordinary skill of the art. Preferably, an amount of cells ranging from a minimum of about 25,000 to a maximum of about $200 \times 10^6$ antigen presenting cells is sufficient. The suspension of cells containing cellular nucleic acid-psoralen monoadducts is returned to the patient according to any appropriate mode of administration known in the art, e.g., injection into the blood stream or the immune system of the patient.

In the preferred embodiments, the method for modifying the immune system response further comprises the step of artificially contacting the mammal's immune system with an antigen for a suitable period of time to stimulate the immune system. As used herein, the term, "artificially stimulate" or "artificially contact" refers to the positive step of contacting and stimulating the immune system of a subject with an antigen through human intervention. The subject (patient, host) to be treated in the present invention is a mammal, preferably a human.

The artificial contacting of the subject's immune system with the specific antigen may be achieved in any manner which introduces the antigen into the subject's immune system,. e.g., by injection directly into the blood stream, the lymphatic system, the lymphoid organs, or the skin. The antigen is then permitted to be in contact with, or exposed to, the subject's immune system, for a suitable time period so as to permit stimulation of certain leukocytes specifically in response to that antigen. This suitable period of time could be as long as one year but in most instances is shorter and generally is no longer than 72 hours.

As used herein, the term antigen refers to any molecule capable of inducing an immune response and includes peptides, nucleoproteins, nucleic acids, polysaccharides and analogues of these molecules. The term analogue includes the above-identified antigens which have been modified, e.g., by chemical agents or enzymatic cleavage, synthetic molecules containing all or part of the above-identified antigens, as well as hybrid molecules, e.g., molecules containing portions of at least two different antigens. The analogues are prepared using chemical or biochemical synthesis methods, e.g., by employing cloning techniques, according to methods within the ordinary skill of the art. In general, an antigen is any molecule which can potentially elicit an immune system response. Thus, the term antigen includes autologous antigens, e.g., circulating tissue antigens associated with an autoimmune disease and cancer antigens that are present in autologous cancer cells but are not expressed in a non-neoplastic state, as well as exogenous antigens.

Preferred antigens include proteins and/or peptides associated with an allergic reaction (e.g., poison ivy, penicillin), a pathological state, an immunodeficiency disease or a hypersensitivity disease. Exemplary immunodeficiency diseases include acquired immunodeficiency syndrome (AIDS), certain forms of cancer, immunodeficiency of old age, and immunodeficiency following immunosuppressive therapy. Hypersensitivity disease is broadly defined to include delayed-type hypersensitivity reaction, autoimmune disease, allergy, infectious disease, rejection of allografts, and graft-versus-host reaction. More specifically, exemplary autoimmune diseases include rheumatoid arthritis, pemphigus vulgaris, systemic sclerosis and systemic lupus erythematosus. Exemplary AIDS-related antigens include core protein p24, envelope protein gp120, gp41, gp55, and gp66/31 (Bisaccia, E. et al., supra.).

Antigens associated with a pathological state, e.g., peptides derived from a solid tumor malignancy, are isolated by surgically removing all or part of the tumor and extracting the tumor-associated antigens. In addition, tissue culture supernatants from suspensions of the malignant cells and plasma of patients with malignancy can serve as sources of the tumor associated antigens. Exemplary cancer antigens include tumor antigens such as those described by P. Boon in "Toward a Genetic Analysis of Tumor Rejection Antigens", *Adv. Cancer Res.* 58:177–210(1992). As disclosed in Boon, supra., exemplary tumor antigens include: P91A, P35B, P198 and P1A and corresponding mutants, disclosed therein.

The term antigen also includes antigens associated with a hypersensitivity disease, and in particular, antigens associated with a hypersensitivity disease mediated by the clonal expansion of circulating aberrant T cells. In a preferred embodiment, the antigen is derived from a clonotypic T cell receptor. The present invention thus provides a method for enhancing a clone-specific immune reaction which kills or inhibits proliferation of an aberrant population of T cells.

Also within the scope of the invention are pharmaceutical compositions for modifying an immune response to an antigen. The composition comprises a pharmacologically acceptable carrier and a preparation of cells containing a plurality of cellular nucleic acid-psoralen monoadducts and substantially no cellular nucleic acid-psoralen crosslinks. In a preferred embodiment, the ratio of psoralen monoadduct to crosslinks is at least about 2 to 1, more preferably, about 10 to 1, and most preferably 49 to 1. Accordingly, the photoactivated cell suspension advantageously contains cells having an enhanced population of non-lethal mutations (caused by the absence of psoralen-crosslinks) in comparison with cells treated using conventional photopheresis procedures, e.g., exposure to psoralen in the presence of ultraviolet A radiation.

Optionally, the pharmaceutical composition further contains a concentration of antigen which is capable of stimulating an immune response. In general, a concentration of antigen up to about 100 ug/ml is preferred although substantially lower antigen concentrations may be used. See e.g., Hosken, N., et al., "Class I-restricted presentation occurs without internalization or processing of exogenous antigenic peptides", *J. Immunology* 142(4):1079–1083 (1989) and Townsend, A., et al., "The epitopes of influenza nucleoprotein recognized by cytotoxic T lymphocytes can be defined with short synthetic peptides", *Cell* 44:959–968 (1986). A determination of the optimum antigen concentration for eliciting an immune response is within the level of skill of the art without undue experimentation.

EXAMPLES

The formation of 8-methoxypsoralen-DNA monoadducts and crosslinks is presumed to be responsible for the efficacy of photochemotherapies that employ 8-methoxypsoralen activated with long wavelength ultraviolet radiation (UVA, 320–400 nm). The following examples demonstrate that 8-methoxypsoralen can also be activated with visible light at 419 nm or 447 nm.

Example 1

Absorption Spectrum of 8-methoxypsoralen (8-MOP).

The absorption spectrum of 8-MOP (Sigma, St. Louis Mo.) dissolved in absolute ethanol (either 0.010 or 10 mg/ml) was recorded from 200–500 nm using an LKB Ultrospec II. Extinction coefficients, derived from the gravimetrically determined molar concentrations, are shown for the following wavelengths: 300, 350, 400, 420 and 450 nm. The concentrations of all diluted solutions were verified either spectrophotometrically or by HPLC analysis (described below).

The absorption spectrum of 8-MOP is plotted with the extinction coefficient on a logarithmic scale in order to illustrate the low but finite absorbance in the visible region (FIG. 2). A comparison of the extinction coefficients at 350 nm and 420 nm (2016 and 0.60$M^{-1}$ respectively) would predict that a nearly 3360-fold greater dose of the latter wavelength energy would be required to deliver the same number of absorbed photons at 350 nm and hence induce a similar number of photoadducts. In fact, a much smaller dose of visible radiation was required to form photoadducts in bovine smooth muscle cells than predicted based upon the relative extinction coefficients at these wavelengths (see Examples 2 and 3).

Example 2

Photodegradation of 8-MOP: Comparison of Visible and Ultraviolet A radiation.

The relative ability of ultraviolet A (UVA) and visible radiation (VIS) to induce 8-MOP photodegradation was measured. 8-MOP (1034 ng/ml) dissolved in ethanol was exposed to doses of either ultraviolet A (UVA) radiation (4.5 mW/cm$^2$, window glass filtered) or 419 nm radiation (6.5 mW/cm$^2$).

The 8-MOP concentration at time zero is indicated by dashed line in FIG. 3. Aliquots (0.25 ml) were taken at 30, 60 and 90 min. and analyzed by HPLC (Gasparro, F. P., et al., "Rapid and sensitive analysis of 8-methoxypsoralen in plasma", *J. Invest. Dermatol.* 90:234–236 (1988)). An exposure of UVA (8 J/cm$^2$) for 30 min. led to 22% 8-MOP degradation. A comparable dose of 419 nm light led to 2.2% degradation. In other studies we have observed that shorter UVA wavelengths (320 and 340 nm, for example) were much more efficient at 8-MOP degradation than longer UVA wavelengths (J. Battista, unpublished results). Thus, the shorter wavelength components of UVA radiation may degrade 8-MOP and may effectively reduce the concentration of drug available for photoreactions with DNA bases. In addition, the shorter UVA wavelengths may effectively reduce the level of photoadduct formation by inducing the photoreversal of already formed photoadducts (Tessman, J. W., et al., "Photochemistry of furan-side 8-methoxypsoralen-thymidine monoadduct inside the DNA helix. Conversion to diadduct and to pyrone-side monoadduct", *Biochem.* 24:1669–1676 (1985)).

Example 3

Formation of Psoralen-DNA Monoadducts in Smooth Muscle Cell Using Visible light (419 nm).

(A) Bovine Aorta Smooth Muscle Cells.

Thoracic aortas were removed aseptically from calves and smooth muscle cells (SMC) were obtained by an explant method. Briefly, the vessels were opened in a laminar flow hood and the endothelial cell layer was mechanically scraped off. Two millimeter punch biopsies of the aorta media layer were obtained and placed in a culture dish with media consisting of Dulbecco's modified Eagle's Medium (DMEM, GIBCO, Grand Island N.Y.) supplemented with 10% (v/v) heat inactivated fetal calf serum, antibiotics (300 units/ml each of penicillin and streptomycin) and 0.2M L-glutamine (GIBCO). The smooth muscle cell biopsies were left at 37° C. in a 5% CO$_2$ incubator until SMC explants were detected. SMC are differentiated from fibroblasts by their appearance during confluency, forming hill and valley morphology whereas the latter produce a whorl type of appearance. In addition, SMC proliferation was inhibited by heparin (0.1 mg/ml) and antibody specific for SMC actin (HHF35, Enzo Diagnostics, New York, N.Y.) was used as an immunologic marker for SMC actin. SMC were sub-cultured with 0.01% trypsin/EDTA and SMC from passages 3 to 7 were used.

(B) Irradiation.

Figure 6:
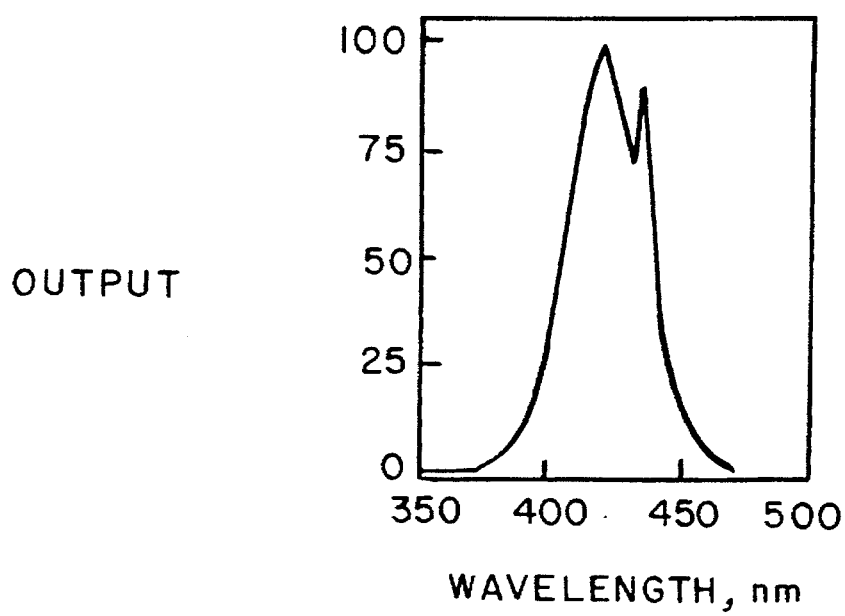
FIG. 6 illustrates the spectral output of the 419 nm lamps used to irradiate a psoralen-cell suspension.

The SMC were incubated with 8-MOP 1050 ng/ml including 0.5–1.5% [$^3$H]8-MOP (specific activity, 83 Ci/mmol; Amersham, Arlington Hts Ill.) in Hank's Balanced Salt Solution (HBSS) for 30 min. in the dark prior to irradiation. A photochemical reactor (Southern New England Ultraviolet Co., Branford, calf thymus) equipped with six 8 watt lamps emitting visible light (centered at 419 nm, ±17 nm at half height) was used to irradiate the cells at a distance of 12.5 cm (the lamps were equally spaced over a 135° angle). An irradiance of 6.5 mW/cm$^2$ was determined using a calibrated silicon diode UV250Bq (EG&G, Montgomeryville Pa.). The spectral output of the 419 nm lamps (FIG. 6) was determined by focusing the light onto a Jarrell-Ash Monospec 27 (Allied Analytical, Waltham Mass.) equipped with an optical spectral multichannel analyzer and a diode array detector (Princeton Instruments, Princeton N.J.).

(C) DNA Isolation.

After treatment with 8-MOP and either visible light or UVA radiation, the cells were washed to remove unbound 8-MOP and any low molecular weight degradation products. The cells were detached from the petri dishes by trypsinization. DNA was isolated as described previously (Bevilacqua, P. M., et al., "High performance liquid Chromatography analysis of 8-methoxypsoralen monoadducts and crosslinks in lymphocytes and keratinocytes", *J. Invest. Dermatol.* 97:151–155 (1991)). The DNA concentration was determined spectrophotometrically at 260 nm after recording the full spectrum from 200 to 400 nm (LKB UltroSpec II. Piscataway N.J.).

(D) Characterization of 8-MOP photoadduct formation.

The specific activity of [$^3$H]8-MOP was used to calculate the extent of photoadduct formation using duplicate 0.020 ml aliquots of the isolated DNA. DNA was hydrolyzed using nucleolytic enzymes and then analyzed by a slightly modified reversed phase HPLC protocol (Bevilacqua, P. M., et al., "High performance liquid Chromatography analysis of 8-methoxypsoralen monoadducts and crosslinks in lymphocytes and keratinocytes", *J. Invest. Dermatol.* 97:151–155 (1991). To each 0.5 ml faction, 4 ml of scintillation fluid (Ecoscint, National Diagnostics, Manville N.J.) was added prior to scintillation analysis (LKB Rack Beta).

Figure 7:
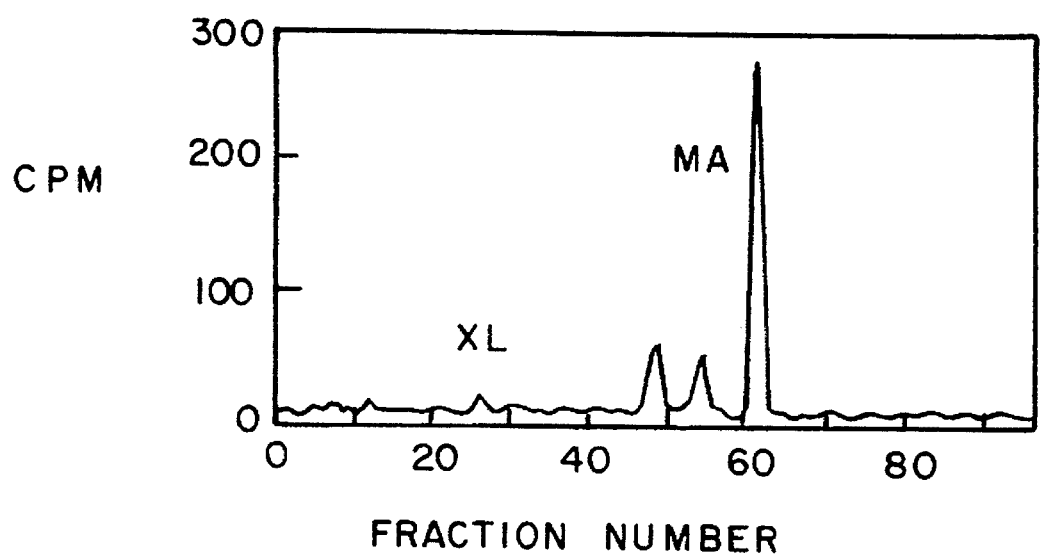
FIG. 7 illustrates HPLC analysis of enzymatically hydrolyzed DNA from smooth muscle cells.

HPLC analysis of enzymatically hydrolyzed DNA from the 419 nm/8-MOP treated SMC is shown in FIG. 7. The pattern of peaks is comparable to that previously found for cells treated with UVA and 8-MOP (Bevilacqua, P. M., et al., "High performance liquid Chromatography analysis of 8-methoxypsoralen monoadducts and crosslinks in lymphocytes and keratinocytes", *J. Invest. Dermatol.* 97:151–155 (1991). The peak eluting near fraction 25 corresponds to the crosslink (XL); the peak near fraction 50, the 3,4-MA (pyrone ring monoadduct); and those at fractions 53–62, the 4',5'-MA (furan ring monoadduct).

(E) Results.

In the case of 419 nm irradiation at 7 J/cm$^2$, the primary photoadduct was the furan ring monoadduct (84.2% yield). The yield of psoralen-crosslink were much lower than those obtained for the cells treated with UVA (Table 1). The reduction in crosslink formation is a result of the relative change in extinction coefficients for 8-MOP and 4',5'-MA beyond 380–390 nm, i.e., the monoadduct is apparently incapable of absorbing a second photon of light at the visible wavelengths to generate the psoralen crosslink.

The treatment of SMC with 1050 ng/ml 8-MOP and 7 J/cm$^2$ 419 nm radiation led to the formation of 9.7 adducts/ megabasepair (mbp) of DNA. At a higher 419 nm intensity (12 J/cm$^2$), a proportionately greater number of photoadducts were formed (the average of two runs was 14.4 adducts; see Table 1). UVA irradiation of the cells at an intensity of 2 J/cm$^2$ led to the formation of 88 photoadduct/ mbp. The linear relation between adduct formation and the product of 8-MOP and UVA doses would predict the formation of 308 adducts/mbp$^5$ using 7/J/cm$^2$. Thus although the ratio of extinction coefficients for the UVA and visible wavelengths was 3360 the ratio of photoadducts fell within a factor of 20 (at 7 J/cm$^2$).

TABLE 1

Adduct Distribution in Cells Treated with 8-MOP

| Irradiation Wavelength | adducts /mbp | Percentage Photoadduct | | |
|---|---|---|---|---|
| | | 4',5'-MA | 3,4,-MA | crosslink |
| 7 J/cm$^2$419nm | 9.7 | 84.2 | 13.3 | 2.5 |
| 12 J/cm$^2$419nm (run 1) | 15.3 | 85.6 | 7.8 | 6.4 |
| 12 J/cm$^2$419nm (run 2) | 13.5 | 77.3 | 11.9 | 10.8 |
| 2 J/cm$^2$UVA | 88.0 | 40.9 | 11.7 | 47.4 |

Example 4

Formation of Psoralen-DNA Monoadducts in Solution: Modification of Calf Thymus DNA with 8-MOP and Visible Light (419 nm and 447 nm).

(A) Materials

Nuclease P$_1$ (EC 3.1.30.1) from *Penicillium citrinum*, deoxyribonuclease I (DNase I; EC 3.1.21.1) from bovine pancreas, and alkaline phosphatase (EC 3.1.3.1) type VII-S from bovine intestinal mucosa in suspension (2–4 U/ul) and calf thymus DNA (highly polymerized) (all from Sigma, St. Louis, Mo.) were used without further purification. Other materials included: [$^3$H]-8MOP (79 Ci/mmol, Amersham, Arlington Heights, Ill.), 8-MOP (Aldrich, Milwaukee, Wis.), triethylamine (Fluka, Ronkonkoma, N.Y.) acetic acid (Fisher Scientific, Pittsburgh, Pa.), Ecoscint scintillation fluid (Ecoscint, National Diagnostics, Manville, N.J.), HPLC grade water and HPLC grade methanol (MeOH) (J. T. Baker, Inc., Phillipsburg, N.J.), and 0.25% Trypsin-EDTA (ethylenediaminetetraacetic acid), Dulbecco's Phosphate Buffered Saline (DPBS), Hank's Balanced Salt Solution (HBSS) (without phenol red), and fetal bovine serum (Gibco BRL, Bethesda, Md.). Other chemicals were reagent grade and used without further purification.

(B) DNA Hydrolysis

The procedure used for DNA hydrolysis was adapted from a procedure reported by Singhal, et al., "High-performance liquid chromatography for trace analysis of DNA and kinetics of DNA modification," *BioChrom.* 4:78–88 (1989). A stock solution containing 1 U/ul Nuclease P$_1$ and 0.1 U/ul DNase I in water and a 10 mM ZnCl$_2$ and 30 uM NaOAc pH 5.3 buffer solution were prepared. The amount of DNA in each sample was determined by measuring the optical density (OD) at 260 nm using an Ultraspec II (Pharmacia LKB). For each OD of DNA in the sample (5 )D maximum, 200 ul maximum volume), one ul of the enzyme stock and 10 ul of the buffer were added (two and twenty ul minimum, respectively), and the sample was incubated at 37° C. for 2 hours. Thereafter, 10 ul of 1M sodium glycinate, pH 8, and 1 ul of alkaline phosphatase were added per OD of DNA (twenty and two ul minimum, respectively), and the sample was incubated at 37° C. for 3 hours. After centrifugation to remove any suspended solids, the samples were directly injected onto the HPLC column for analysis.

(C) HPLC Analysis

A Regis Rexchrom ODS (octyldecylsilyl) column (4.6× 250 mm, 5 micron, Regis, Morton Grove, Ill.) was used in conjunction with a Spectra-Physics (San Jose, Calif.) SP8800 ternary HPLC equipped with a Spectra-Focus forward optical scanning detector (200–360 nm) and Spectra Focus Software package for detection and integration. Injections were made using a Rheodyne 7125 injection port and eluting fractions were collected (Frac-100, Pharmacia LKB, Piscataway, N.J.) at 0.5 min intervals (flow rate=1 ml/min) into scintillation vials (Simport, American Bioanalytical, Natick, Mass.). Scintillation analysis was performed by adding 4 ml scintillation fluid to each fraction and counting on a Beta counter (60 second count, RacBeta, Pharmacia LKB). The relative percent of each component detected was determined by summing the counts associated with that component (minus background) and dividing by the total counts. The eluents and gradients used are listed in Table 2.

TABLE 2

HPLC MOBILE PHASE GRADIENT CONDITIONS

| eluent A: | MeOH | | | flow rate: 1.0 ml/min | | | | |
|---|---|---|---|---|---|---|---|---|
| eluent B: | 0.1M triethylammonium acetate pH 6.8 fraction size: 0.5 min | | | | | | | |
| gradient: | | | | | | | | |
| time (min) | 0.0 | 0.1 | 3.5 | 16.0 | 23.0 | 33.0 | 36.0 | 38.7 | 41.0 |
| % A | 5.5 | 9.0 | 15.7 | 25.5 | 25.5 | 32.5 | 32.5 | 35.5 | 100.0 |
| % B | 94.5 | 91.0 | 84.3 | 74.5 | 74.5 | 67.5 | 67.5 | 64.5 | 0.0 |

(D) Photoadduct Formation in Calf Thymus DNA

Figure 8:
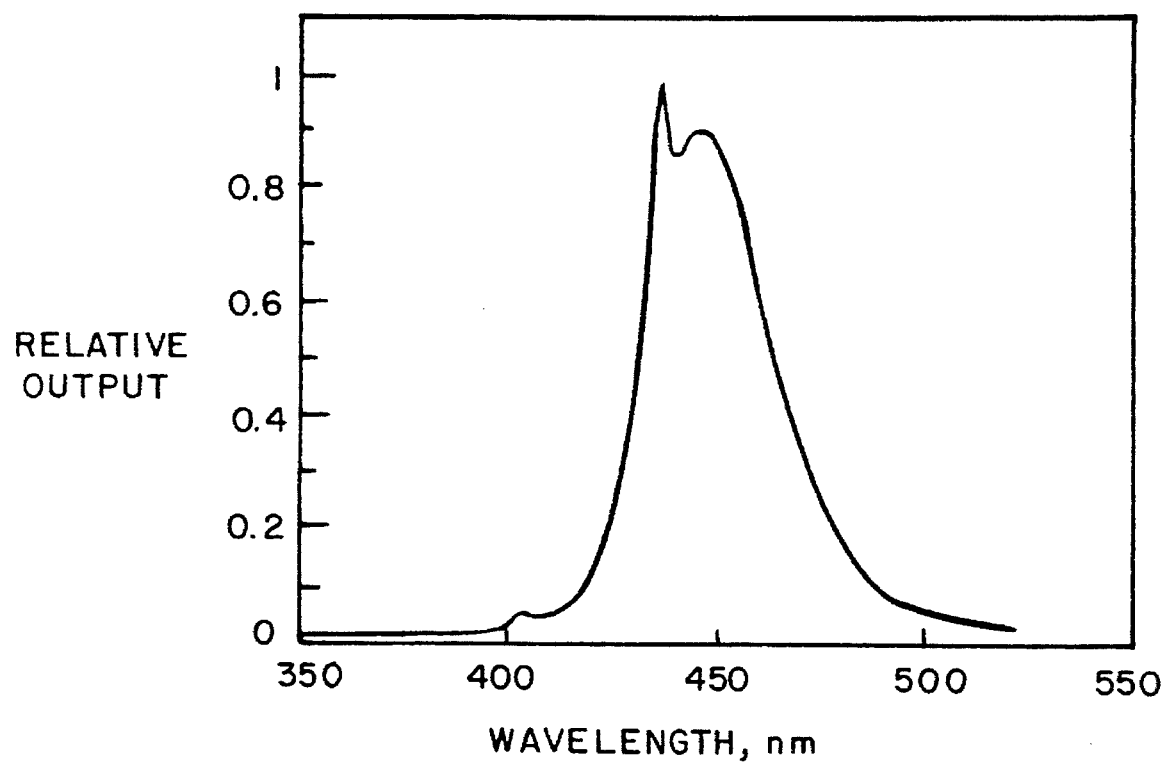
FIG. 8 illustrates the spectral output of the 447 nm lamps used to irradiate a psoralen-cell suspension.

Solutions of Calf thymus DNA (10 OD/ml, 1.54 mM), 8-MOP (180 uM) and [$^3$H]8-MOP (1 ul/100 ul) were prepared in 10 mM Tris, 1 mM EDTA and 0.1M NaCl, pH 7.8, and three 5 ul aliquots removed for scintillation analysis for specific activity measurements. A 300 ul aliquot was irradiated at 419 nm (with a 17 nm bandwidth) for 1.0 or 4.0 hours at 4° C. using a fluorescent lamp emitting at 419 nm. Irradiations were also performed on 300 ul aliquots at 447 nm (20 nm bandpass) for 1.0 or 4.0 hours. The spectral output of the 419 nm (FIG. 6) and 447 nm (FIG. 8) lamps was determined by focusing the light onto a Jarrell-Ash Monospec 27 (Allied Analytical, Waltham, Mass.) equipped with an optical spectral multichannel analyzer and a diode array detector (Princeton Instruments, Princeton, N.J.). The samples were precipitated and washed twice, as described above, and then redissolved to their original volume with HPLC water. Aliquots were removed for ultraviolet spectroscopic and scintillation analyses to determine binding levels (as above), and 20 ul aliquots from each sample were removed and digested for HPLC analysis. Solutions of 1.54 mM Calf thymus DNA, [$^3$H]8-MOP, and either 50, 100 or 200 uM 8-MOP were prepared in the standard buffer for concentration studies, with aliquots removed from each sample for scintillation analysis to determine specific activity. The samples were precipitated and washed twice, then analyzed as above.

Irradiation of calf thymus-DNA (1.54 mM) and [$^3$H]-8-MOP (180 uM) with 419 nm led to the formation of 1.28 (1 hour) and 4.48 (4 hours) adducts/kilobase, with the adducts detected by digestion and HPLC analysis (See Table 3, this Example). The distribution of adducts at 1 hour was: 0% crosslink; 5.8% 3,4-monoadduct and 94.2% 4',5'-monoadduct. At 4 hours irradiation at 419 nm, the distribution of adducts was: 6.4% crosslink; 9.7% 3,4-monoadduct; and 83.9% 4', 5'-monoadducts.

Irradiation of calf-thymus-DNA as above, but with 447 nm light, led to the formation of 0.109 (1 hour and 0.446 (4 hours) adducts/kilobase. The distribution of adducts at 1 hour was: 0% crosslinks, 0% 3,4-monoadducts and 100% 4'5'-monoadducts. At 4 hours irradiation at 447 nm, the distribution of adducts was: 1.7% crosslinks; 7.5% 3,4monoadducts; and 90.8% 4',5'-monoadducts. As expected, the major photoadduct formed was the furan-ring monoadduct (4',5'-monoadduct).

Irradiation of the calf thymus-DNA and [$^3$H]-8-MOP at two different visible wavelengths led to the formation primarily of monoadducts with a small percentage of crosslinks, as determined by digestion and HPLC analysis. In absolute, terms the extent of adduct formation, as well as the amount of each adduct, increased steadily with increasing irradiation. The increase in monoadduct formation at 447 nm and one hour irradiation indicates not only that visible light can be used to activate psoralen but that a combustion of irradiation parameters may be selected to obtain the most desired distribution of photoadducts in the treated cell suspension.

TABLE 3

Distribution of Photoadducts Following
419 and 447 nm treatment of DNA with 8-MOP

| | adducts /kb | Cross link | 3,4 monoadduct | 4',5' monoadduct |
|---|---|---|---|---|
| 419 nm | | | | |
| 1 hour | 1.28 | 0 | 5.8 | 94.2 |
| 4 hour | 4.48 | 6.4 | 9.7 | 83.9 |
| 447 nm | | | | |
| 1 hour | 0.109 | 0 | 0 | 100 |
| 4 hour | 0.446 | 1.7 | 7.5 | 90.8 |

Lamp output: 419 nm 6.4 mW/cm$^2$
447 nm 5.6 mW/cm$^2$
Note: Using UVA roughly 50% of the adducts would be crosslinks (XL).

It should be understood that the preceding is merely a detailed description of certain preferred embodiments. It therefore should be apparent to those skilled in the art that various modifications and equivalents can be made without departing from the spirit or scope of the invention.

What is claimed is:

1. A method for forming a suspension of leukocyte cells containing cellular nucleic acid-psoralen monoadducts, the method comprising the steps of:

(a) contacting a suspension of leukocyte cells containing cellular nucleic acid molecules with a plurality of psoralen molecules to form a psoralen-cell suspension; and (b) extracorporeally irradiating the psoralen-cell suspension with visible light having a wavelength greater than about 420 nm to form a plurality of cellular nucleic acid-psoralen photoadducts including monoadducts and crosslinks, wherein the ratio of the monoadducts to crosslinks is at least about 10 to 1.

2. A method as claimed in claim 1, wherein the psoralen-cell suspension is irradiated with visible light to form the suspension of cells, wherein the ratio of the monoadducts to crosslinks is at least about 49 to 1.

3. A method as claimed in claim 1, wherein the step of irradiating comprises irradiating the psoralen-cell suspension with visible light having a wavelength of about 450 nm and an intensity of about 6 mW/cm$^2$ for about 1 to about 3 hours.

4. A method as claimed in claim 1, wherein the step of irradiating comprises irradiating the cells with a helium/cadmium laser emitting radiation at 442 nm.

5. A method as claimed in claim 1, wherein the leukocyte cells are T cells.

6. A method as claimed in claim 1, wherein the psoralen is selected from the group consisting of 8-methoxypsoralen, aminomethyltrimethylpsoralen, 5-methoxypsoralen and trimethylpsoralen.

7. A method as claimed in claim 6, wherein the psoralen is 8-methoxypsoralen.

8. A method as claimed in claim 1, wherein the cellular nucleic acid is DNA.

9. A method for making a pharmaceutical preparation for administration to a mammal, comprising the steps of:

(a) contacting a suspension of leukocyte cells containing cellular nucleic acid molecules with a plurality of psoralen molecules to form a psoralen-cell suspension;

(b) extracorporeally irradiating the psoralen-cell suspension with visible light having a wavelength greater than about 420 nm to form a plurality of cellular nucleic acid-psoralen photoadducts including monoadducts and crosslinks, wherein the ratio of the monoadducts to crosslinks is at least about 10 to 1; and (c) placing the irradiated psoralen-cell suspension in a pharmaceutically acceptable carrier.

10. A method as claimed in claim 9, wherein the psoralen-cell suspension is irradiated with visible light to form the suspension of cells, wherein the ratio of the monoadducts to crosslinks is at least about 49 to 1.

11. A method as claimed in claim 9, wherein the step of irradiating comprises irradiating the psoralen-cell suspension with visible light having a wavelength of about 450 nm and an intensity of about 6 mW/cm$^2$, for about 1 to about 3 hours.

12. A method as claimed in claim 9, wherein the step of irradiating comprises irradiating the cells with a helium/cadmium laser emitting radiation at 442 nm.

13. A method for modifying the immune system response of a mammal to an antigen, comprising the steps of:

(a) withdrawing a suspension of leukocyte cells containing cellular nucleic acid molecules from a mammal that has been exposed to the antigen;

(b) contacting the suspension of leukocyte cells containing cellular nucleic acid molecules with a plurality of psoralen molecules to form a psoralen-cell suspension;

(c) extracorporeally irradiating the psoralen-cell suspension with visible light having a wavelength greater than about 420 nm to form a plurality of cellular nucleic acid-psoralen photoadducts including monoadducts and crosslinks, wherein the ratio of the monoadducts to crosslinks is at least about 10 to 1;

(d) placing the irradiated psoralen-cell suspension in a pharmaceutically acceptable carrier to form a pharmaceutical preparation for modifying the immune response; and (e) administering the pharmaceutical preparation to the mammal so as to modify the immune system response of the mammal to the antigen.

14. A method as claimed in claim 13, wherein the psoralen-cell suspension is irradiated with visible light to form the suspension of cells, wherein the ratio of the monoadducts to crosslinks is at least about 49 to 1.

15. A method as claimed in claim 13, wherein the step of irradiating comprises irradiating the psoralen-cell suspension with visible light having a wavelength of about 450 nm and an intensity of about 6 mW/cm$^2$, for about 1 to about 3 hours.

16. A method as claimed in claim 13, wherein the step of irradiating comprises irradiating the cells with a helium/cadmium laser emitting radiation at 442 nm.

17. A method as claimed in claim 13, wherein the cells are T cells.

18. A method as claimed in claim 13, wherein the psoralen is selected from the group consisting of 8-methoxypsoralen, aminomethyltrimethylpsoralen, 5-methoxypsoralen and trimethylpsoralen.

19. A method as claimed in claim 18, wherein the psoralen is 8-methoxypsoralen.

20. A method as claimed in claim 13, wherein the cellular nucleic acid molecule is DNA.

21. A method as claimed in claim 13, wherein the mammal is a human.

22. A pharmaceutical composition for modifying an immune system response to an antigen, comprising:

a preparation of leukocyte cells wherein the preparation of leukocyte cells has been prepared by irradiating leukocyte cells with visible light having a wavelength greater than about 420 nm, the leukocyte cells containing a plurality of cellular nucleic acid-psoralen photoadducts including monoadducts and crosslinks, wherein the ratio of the monoadducts to crosslinks is at least about 10 to 1; and a pharmaceutically acceptable carrier.

23. A pharmaceutical composition as claimed in claim 22, wherein the ratio of cellular nucleic acid-psoralen monoadducts to nucleic acid-psoralen crosslinks is at least about 49 to 1.

* * * * *

UNITED STATES PATENT AND TRADEMARK OFFICE
CERTIFICATE OF CORRECTION

PATENT NO. : 5,462,733
DATED : 10/31/95
INVENTOR(S) : Francis Gasparro, Richard Edelson It is certified that error appears in the above-identified patent and that said Letters Patent is hereby corrected as shown below:

Column 1, line 4, insert the following:

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Twentieth Day of April, 1999

Attest:

Q. TODD DICKINSON

*Attesting Officer*     *Acting Commissioner of Patents and Trademarks*